US009265576B2

(12) United States Patent
Srinivasan

(10) Patent No.: US 9,265,576 B2
(45) Date of Patent: *Feb. 23, 2016

(54) LASER GENERATOR FOR MEDICAL TREATMENT

(71) Applicant: C Laser, Inc., Lebanon, IN (US)

(72) Inventor: Pattanam Srinivasan, Lebanon, IN (US)

(73) Assignee: C Laser, Inc., Lebanon, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/727,140

(22) Filed: Jun. 1, 2015

(65) Prior Publication Data
US 2015/0257831 A1    Sep. 17, 2015

Related U.S. Application Data

(63) Continuation-in-part of application No. 13/329,596, filed on Dec. 19, 2011, now Pat. No. 9,044,594, which is a continuation-in-part of application No. 13/022,178, filed on Feb. 7, 2011, which is a continuation-in-part of application No. 12/631,835, filed on Jan. 8, 2010, now Pat. No. 9,149,647.

(51) Int. Cl.
A61N 5/06    (2006.01)
A61B 18/22   (2006.01)
(Continued)

(52) U.S. Cl.
CPC ............. *A61B 18/22* (2013.01); *A61B 19/56* (2013.01); *A61D 1/00* (2013.01); *A61N 5/0601* (2013.01); *A61B 2017/00172* (2013.01); *A61B 2018/00434* (2013.01); *A61B 2018/00577* (2013.01);
(Continued)

(58) Field of Classification Search
CPC .............. A61N 2005/0644; A61N 2005/0659; A61N 2005/067; A61N 5/0616
USPC ........................................................ 606/2–19
See application file for complete search history.

(56) References Cited

U.S. PATENT DOCUMENTS 4,566,438 A    1/1986  Liese
4,959,063 A    9/1990  Kojima
(Continued)

FOREIGN PATENT DOCUMENTS

DE    4429192 A1    2/1996
DE    20003349 U1   6/2000
(Continued)

OTHER PUBLICATIONS

U.S. Final Office Action for U.S. Appl. No. 13/022,178 dated Sep. 24, 2015, 13 pages.
(Continued)

Primary Examiner — Aaron Roane
(74) Attorney, Agent, or Firm — Fish & Richardson P.C.

(57) ABSTRACT

A laser generator for laser therapy in the treatment of pain conditions by selective destruction of nociceptive or pain nerves, where a laser generator that generates a continuous and pulsed wavelength that is transmitted fiber-optically through a laser fiber within a spinal needle to contact areas within a body where pain nerves require destruction through optical absorption of laser energy by pain nerves without affecting other types of nerves or surrounding tissues. The laser generator can be used for treatment in humans, small animals and also large animals, which can receive pain relief without adverse effects.

20 Claims, 3 Drawing Sheets

(51) Int. Cl.
*A61B 19/00* (2006.01)
*A61D 1/00* (2006.01)
*A61B 18/00* (2006.01)
*A61B 18/20* (2006.01)
*A61B 17/00* (2006.01)

(52) U.S. Cl.
CPC ............ *A61B2018/00642* (2013.01); *A61B 2018/00708* (2013.01); *A61B 2018/2005* (2013.01); *A61N 2005/0612* (2013.01); *A61N 2005/0626* (2013.01); *A61N 2005/0662* (2013.01)

(56) References Cited

U.S. PATENT DOCUMENTS

| | | | |
|---|---|---|---|
| 5,464,436 | A | 11/1995 | Smith |
| 5,514,126 | A | 5/1996 | Prescott |
| 5,772,597 | A | 6/1998 | Goldberger |
| 5,807,261 | A | 9/1998 | Benaron |
| 6,080,148 | A | 6/2000 | Damasco |
| 6,267,779 | B1 | 7/2001 | Gerdes |
| 6,519,485 | B2 | 2/2003 | Wiesmann et al. |
| 6,663,659 | B2 | 12/2003 | McDaniel |
| 6,921,413 | B2 | 7/2005 | Mahadevan-Jansen et al. |
| 6,942,658 | B1 | 9/2005 | Rizoiu et al. |
| 7,976,571 | B2 | 7/2011 | Neuberger |
| 2001/0056278 | A1 | 12/2001 | Nield et al. |
| 2002/0045922 | A1 | 4/2002 | Nield et al. |
| 2002/0182186 | A1 | 12/2002 | Loeb |
| 2003/0028147 | A1 | 2/2003 | Ayes et al. |
| 2003/0120267 | A1 | 6/2003 | Kaufman |
| 2003/0225331 | A1 | 12/2003 | Diederich |
| 2004/0014199 | A1 | 1/2004 | Streeter |
| 2004/0082942 | A1 | 4/2004 | Katzman |
| 2005/0049582 | A1 | 3/2005 | DeBenedictis |
| 2005/0065577 | A1 | 3/2005 | McArthur |
| 2005/0182293 | A1 | 8/2005 | Katzman |
| 2005/0283148 | A1 | 12/2005 | Janssen et al. |
| 2007/0162093 | A1 | 7/2007 | Porter |
| 2007/0179485 | A1 | 8/2007 | Yeik |
| 2008/0027520 | A1 | 1/2008 | Choi |
| 2008/0077198 | A1 | 3/2008 | Webb |
| 2008/0091249 | A1 | 4/2008 | Wang |
| 2008/0125836 | A1 | 5/2008 | Streeter |
| 2008/0249517 | A1 | 10/2008 | Svanberg |
| 2009/0069673 | A1 | 3/2009 | Tapalian |
| 2009/0125036 | A1 | 5/2009 | Bleich |
| 2009/0299349 | A1 | 12/2009 | Kubota |
| 2010/0016783 | A1 | 1/2010 | Bourke et al. |
| 2010/0152715 | A1 | 6/2010 | Srinivasan |
| 2011/0196357 | A1 | 8/2011 | Srinivasan |
| 2011/0218524 | A1 | 9/2011 | Cattaneo |
| 2011/0301581 | A1 | 12/2011 | Thyzel |
| 2012/0089135 | A1 | 4/2012 | Srinivasan |
| 2013/0281839 | A1 | 10/2013 | Jain et al. |
| 2014/0243806 | A1 | 8/2014 | Srinivasan |

FOREIGN PATENT DOCUMENTS

| | | | |
|---|---|---|---|
| JP | 2009207605 | A | 9/2009 |
| KR | 100963395 | B1 | 6/2010 |
| WO | WO 98/33557 | | 8/1998 |
| WO | WO0162171 | A1 | 8/2001 |
| WO | WO0057804 | A9 | 10/2001 |

OTHER PUBLICATIONS

International Search Report and Written Opinion in International Application No. PCT/US2015/025870, mailed Jul. 24, 2015, 9 pages.

U.S. Notice of Allowance in U.S. Appl. No. 12/631,835, dated Jul. 9, 2015, 17 pages.

"Local Anesthetic," Wikipedia, the free encyclopedia, downloaded from the internet on Nov. 17, 2012, 10 pages http://en.wikipedia.org/wiki/Local_anesthetic.

Schenk et al.; Percutaneous Laser Disk Decompression: A Review of Literature; AJNR 27; Jan. 2006; www.ajnr.org.

Singh et al.; Percutaneous Lumbar Laser Disc Decompression: A Systematic Review of Current Evidence; Pain Physician 2009; 12:573-588 ISSN 1533-3159: www.painphysicianjournal.com.

Tsai et al.; Plasma-mediated ablation: an optical tool for submicrometer surgery on neuronal and vascular systems; Science Direct, Current Opinion in Biotechnology 2009, 20:1-10; www.sciencedirect.com.

Turgut et al.; Extensive Damage to the End-Plates as a Complication of Laser Discectomy an Experimental Study Using an Animal Model; Acta Neurochirurgical 1997; 139: 404-410.

PCT Notification of Transmittal of the International Search Report and the Written Opinion of the International Searching Authority, or the Declaration issued in PCT/US2011/064376 on Feb. 6, 2012, 7 pages.

PCT International Preliminary Report on Patentability for Application No. PCT/US2011/064376 dated Aug. 13, 2013, 7 pages.

PCT Notification of Transmittal of the International Search Report and the Written Opinion of the International Searching Authority, or the Declaration issued in PCT/US2011/066006 on Apr. 19, 2012, 7 pages.

PCT International Preliminary Report on Patentability for Application No. PCT/US2011/066006 dated Aug. 13, 2013, 7 pages.

European Office Action in Application No. 11858106.5, dated Sep. 2, 2014, 5 pages.

European Search Report in Application No. 11858106.5, dated Aug. 21, 2014, 3 pages.

European Search Report issued in Application No. 11858224.6 on Feb. 27, 2015, 3 pages.

Communication Pursuant to Article 94(3) EPC issued in EP 11858224.6 on Mar. 19, 2015, 5 pages.

U.S. Non-Final Office Action for U.S. Appl. No. 12/631,835 dated Dec. 20, 2011, 12 pages.

U.S. Final Office Action for U.S. Appl. No. 12/631,835 dated Jun. 19, 2012, 19 pages.

U.S. Non-Final Office Action for U.S. Appl. No. 12/631,835 dated Sep. 4, 2012, 26 pages.

U.S. Final Office Action for U.S. Appl. No. 12/631,835 dated Mar. 14, 2013, 31 pages.

U.S. Non-Final Office Action for U.S. Appl. No. 12/631,835 dated Mar. 14, 2014, 30 pages.

U.S. Final Office Action for U.S. Appl. No. 12/631,835 dated Jan. 12, 2015, 23 pages.

U.S. Non-Final Office Action for U.S. Appl. No. 13/022,178 dated Dec. 20, 2011, 11 pages.

U.S. Non-Final Office Action for U.S. Appl. No. 13/022,178 dated Aug. 17, 2012, 13 pages.

U.S. Final Office Action for U.S. Appl. No. 13/022,178 dated Feb. 13, 2013, 14 pages.

U.S. Non-Final Office Action for U.S. Appl. No. 13/022,178 dated Jan. 30, 2014, 18 pages.

U.S. Final Office Action for U.S. Appl. No. 13/022,178 dated Jul. 17, 2014, 15 pages.

U.S. Non-Final Office Action for U.S. Appl. No. 13/022,178 on Apr. 23, 2015, 19 pages.

U.S. Non-Final Office Action for U.S. Appl. No. 13/329,596 dated Nov. 14, 2013, 16 pages.

U.S. Notice of Allowance in U.S. Appl. No. 13/329,596, dated Sep. 23, 2014, 10 pages.

U.S. Notice of Allowance in U.S. Appl. No. 13/329,596, dated Dec. 24, 2014, 14 pages.

LASER GENERATOR FOR MEDICAL TREATMENT

CROSS-REFERENCE TO RELATED APPLICATIONS

This application is Continuation-in-Part of U.S. patent Ser. No. 13/329,596 filed Dec. 19, 2011, which is a Continuation-in-Part of U.S. patent application Ser. No. 13/022,178, filed Feb. 7, 2011, which is a Continuation-in-Part of U.S. patent application Ser. No. 12/631,835, filed Jan. 8, 2010, the entirety of each of which are herein incorporated by reference.

TECHNICAL FIELD

This application relates to laser medical devices and its use in medical treatment.

BACKGROUND

Low level laser therapy (LLLT), also known as photobiomodulation, cold laser therapy, and laser biostimulation, is a medical and veterinary treatment, which uses low level lasers or light-emitting diodes to stimulate or inhibit cellular function. LLLT uses light sources such as lasers or LEDs to deliver light of certain wavelengths at certain intensities to affect tissue regeneration, inflammation, or pain. Existing deep tissue lasers today use heat generation to cause a non-selective action destroying non-specific tissue on contact.

SUMMARY

The present disclosure relates to laser generating medical devices that deliver laser energy to nerve endings deep within the body to alleviate pain in a technique known as deep tissue low intensity laser neuro-ablation, as more fully described in the related applications incorporated herein by reference.

In general, one aspect of the subject matter described in this specification may include using a low intensity laser generator to generate a deep tissue low intensity laser (DT-LIL) capable of causing selective destruction of deep nociceptive nerves in large animals. The low intensity laser generator provides the use of deep tissue low intensity laser treatment (DT-LILT) to selectively destroy nerve cells on contact using absorption and cell resonance. The laser generator provides a laser power output that does not generate sufficient heat to destroy surrounding tissue, allowing selective destruction when nerve cells selectively absorb the DT-LILT wavelength. Thus, the laser generator allows for selective deep tissue low intensity laser ablation (DT-LILA) of the nerves, or deep tissue low intensity laser neuroablation (DT-LILNA).

In some implementations, a laser generator may be used in DT-LILT for selectively destroying pain, or nociceptive, nerves in animals. For example, the laser generator generates a continuous and pulsed laser wavelength between either 690 nano-meters (nm) and 980 nm, or 440 and 460 nm, which is transmitted fiber-optically through a laser fiber within a spinal needle to contact areas in the animal body where pain nerves require destruction through optimal absorption of laser energy without affecting other types of nerves or surrounding tissue.

In some implementations, the laser generator may be used in small animals, such as dogs or cats, by generating lasers with average laser power output between 1 mW (milli-watt) to 6 mW. Laser power output in these ranges, which are also typically used in humans, may cause selective destruction when used with the wavelength ranges described above.

In other implementations, the laser generator may be used in larger animals, such as horses or cattle, that may require higher average laser power output due to a higher body weight compared to humans and smaller animals. In some instances, power settings used for large animals may be several magnitudes larger than those used in smaller animals and proportional to the increase in body weights of the larger animals compared to the body weights of smaller animals and humans. Low power lasers that are used for DT-LILT typically have power output within 1 watt (W) (or 1000 milli-watts (mW)). In some implementations, the laser generator has power settings that allow for the generation of a laser with power outputs between 7 mW and 500 mW depending on the proportional increase in body weight of the larger animals where DT-LIL is performed. Accordingly, the laser generator described within this disclosure may be used to generate more suitable low intensity laser power outputs for use on large animals that require the treatment of a chronic pain conditions through DT-LILT by selectively destroying nociceptive nerves in animal tissue.

In a general aspect, a laser generator includes an electronic modulator that is configured to generate one of a continuous non-pulsed signal or a pulsed signal including a wavelength in a specified range. The laser generator also includes a laser unit that is configured to generate a laser, where the laser unit is coupled to the electronic modulator such that the laser generator outputs laser energy that is one of a continuous non-pulsed laser power output or a pulsed laser power output. The laser power output includes a wavelength in the specified range. The laser generator includes an electronic timer controller that is configured to be activated during operation of the laser unit and operable to limit delivery time of the laser. The laser generator further includes a watchdog circuit that is configured to terminate the laser that is output by the laser generator by interrupting power source to the laser unit in response to a determination that the electronic timer controller has failed.

Implementations may include one or more of the following features. The wavelength of the laser power output may be between 700 nanometers (nm) and 705 nm. The wavelength of the laser power output may be between 400 nm and 705 nm. The electronic modulator may be configured to generate the pulsed power output including a pulse width in a range of nanoseconds. The laser generator may be operable to output the pulsed laser power output including a 33 megahertz (MHz) high frequency pulsation and a pulse width that is one of 15 nanoseconds or 24 nanoseconds.

The laser generator may include a power source that is configured to output power within a range between one of 1-6 milli-watts (mW), 7-24 mW, or up to 500 mW. The range may be selected based on a size of the body to be treated.

The laser generator may be operable to output an average power in a range of 12 mW with a peak power in a range of 24 mW associated with the pulsed laser power output that includes the 33 MHz high frequency pulsation and the pulse width of 15 nanoseconds. Additionally or alternatively, the laser generator may be operable to output an average power in a range of 19.2 mW with a peak power in a range of 24 mW associated with the pulsed laser power output that includes the 33 MHz high frequency pulsation and the pulse width of 24 nanoseconds. The power source may include a rechargeable battery.

The laser generator may include a user interface, where operation of the laser generator is controllable via user inputs provided through the user interface. The user interface may include a touchscreen user interface.

The laser generator may include a user-operated shutoff button for emergency shutdown. The laser generator also may include a microcontroller, where the electronic modulator and the electronic timer are included in the microcontroller. The microcontroller may include a power unit that is configured to control an amount of power that is provided to the laser unit.

The laser unit may include a first input that is configured to receive power from the power unit, and a second input that is configured to receive one of the continuous non-pulsed signal or the pulsed signal from the electronic modulator. The laser unit may be operable to output the laser power output with power in a range between one of 1-6 mW, 7-24 mW, or in a range up to 500 mW.

The electronic timer controller may be operable to limit the time delivery time of the laser to one of 5 seconds or 10 seconds. The specified range of the wavelength may be between 690 nm and 980 nm.

The laser generator may include a fiber port that is configured to couple a fiber optic delivery system to the laser generator, and transmit the laser that is output by the laser generator to the fiber optic delivery system for delivery to a treatment area.

The watchdog circuit may be configured to monitor the delivery time of the laser and compare the delivery time of the laser to a predetermined threshold. The watchdog circuit may be configured to determine, in response to the comparing, whether the delivery time of the laser exceeds the predetermined threshold. Based on determining that the delivery time of the laser exceeds the predetermined threshold, the watchdog circuit may determine that the electronic timer controller has failed. In response to determining that the electronic timer controller has failed, the watchdog circuit may terminate the laser that is output by the laser generator.

The laser power output may be configured for application to large animals. The laser generator configured for application on large animals may include a power source that is configured to output power proportional to the weight of the large animal.

The details of one or more implementations are set forth in the accompanying drawings and the descriptions below. Other potential features and advantages will become apparent from the description, the drawings, and the claims.

DEFINITION OF TERMS

1. LILA: Low Intensity Laser Ablation
2. DT-LILT: Deep Tissue Low Intensity Laser Treatment or Therapy.
3. DT-LIL: Deep Tissue Low Intensity Laser.
4. DT-LILA: Deep Tissue Low Intensity Laser Ablation.
5. DT-LILNA: Deep Tissue Low Intensity Laser Neuroablation.

The use of terms DT-LILT, DT-LIL and DT-LILA was first described in co-pending U.S. patent application Ser. No. 12/631,835 entitled "Method for Deep Tissue Laser Treatments Using Low Intensity Laser Therapy Causing Selective Destruction of Nociceptive Nerves." LILA or Low Intensity Laser Ablation, as used herein, is used as a general term identifying ablation or destruction of tissues using a low intensity laser. In general, each of the above terms are synonymous with each other. They can be used and interpreted with the same meaning.

BRIEF DESCRIPTION OF THE DRAWINGS

In the drawings, like reference numbers represent corresponding parts throughout.

DETAILED DESCRIPTION

Figure 1:
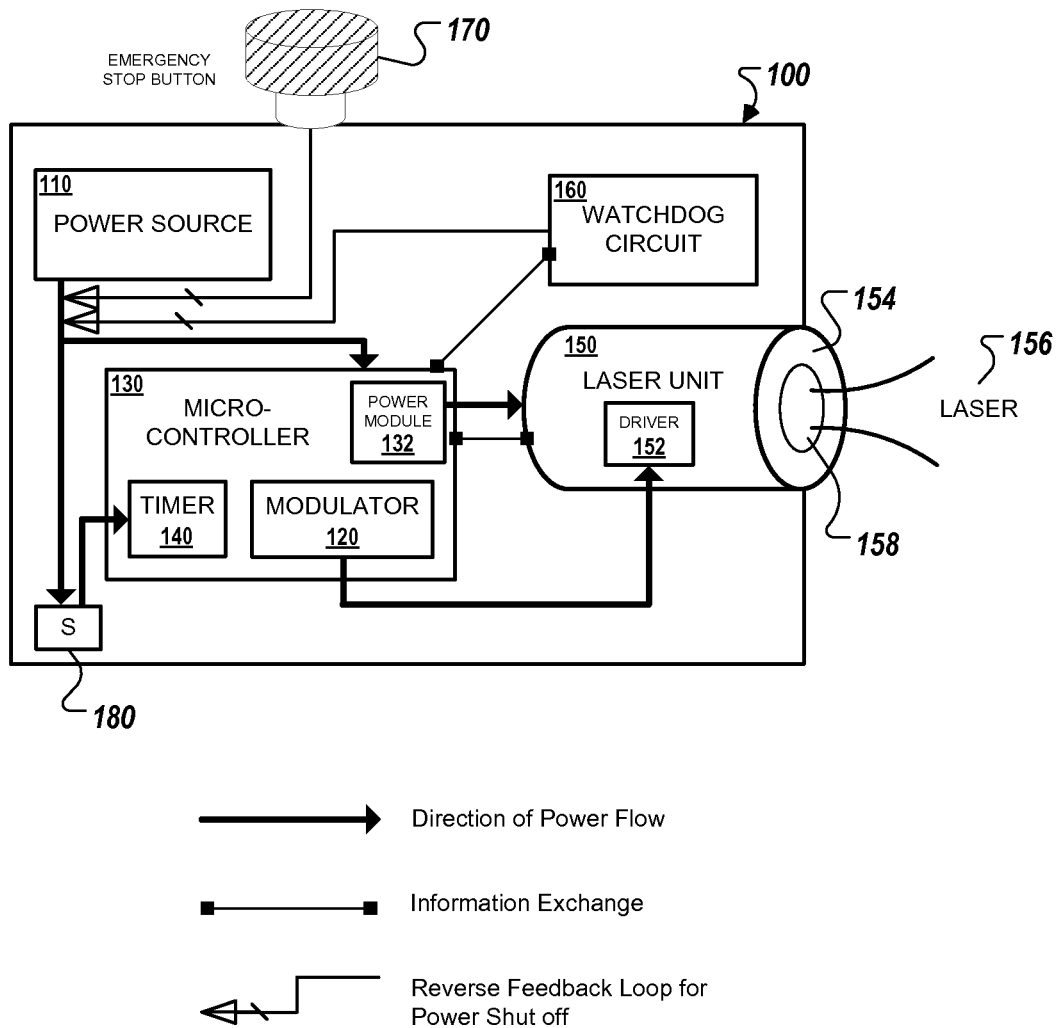
FIG. 1 illustrates a schematic diagram of a laser generator.

Veterinary clinical practices are generally classified as either "small animal practices" or a "large animal practices." In this context, the small animal practices are applied to household pets such as dogs and cats, while large animal practices are applied to non-household animals such as horses, cattle, and wild animals held in captivity (e.g., in zoos). The small and large animals referred throughout this disclosure are defined by the descriptions provided here, and as generally applied in standard veterinary clinical practices. In some instances, the term "intermediate animal" may be used to describe animals that are neither classified as large animals nor small animals, such as pigs, that are maintained in a farm.

Current use of laser generators focus on generating lasers that primarily affect target tissue through heat generation and may often can cause damage to the target tissue. For example, in Coherent Anti-Strokes Raman Spectroscopy (CARS) microscopy, where lasers may be used to observe live tissues, including nerve cells, at near-infrared (NIR) wavelengths, use of lasers often result in cellular plasma expansion and cell disruption resulting from absorbed laser energy by the target tissues. Other examples include experiments that have documented that round worm never cells have been destroyed after applying ultrafast lasers at NIR wavelengths. Due to the potential for tissue damage caused by these laser effects, such microscopic lasers are not currently usable for treatment in clinical settings, except the laser as described in the co-pending parent U.S. patent application Ser. No. 12/631,835, titled "Method for Deep Tissue Laser Treatments Using Low Intensity Laser Therapy Causing Destruction of Nociceptive Nerves" and also as described in this disclosure.

In some instances, use of the low power laser generator in DT-LILT as described in this disclosure and the referenced applications enables the therapeutic use of lasers by putting them in direct and precise contact with the area of treatment even though such treatment areas may lie quite deep within the human body. In some implementations, the destruction of small pain nerves may be achieved within a short time period of laser contact at the area of treatment. The time period may be, for example, five seconds. In such instances, the nerve cell destruction takes place within a fraction of a second after contact, enabling the five-second exposure to be supra maximal or more than optimal. The small pain nerves, which are also known as C pain fibers, do not have myelin sheaths, the outer covering present in other types of nerves. Lack of this myelin sheath or having a thin insignificant outer membrane makes these nerves susceptible to low power laser energy.

The sizes of nerve cells, for example, the nociceptive pain nerves, vary in different animals. For example, nociceptive pain nerves or C pain fibers are proportionally larger in size in larger animals as compared to those found in smaller animals and humans. However, although the nociceptive pain cells in large animals are proportionately larger than those in smaller animals, they are still just as susceptible to laser absorption because they similarly lack myelin sheaths.

Nerve cell composition also plays a significant role in creating susceptibility to laser absorption. For example, flavins, a type of proteins present in nerve cells, may make the nerve cells susceptible to laser absorption at wavelengths between 440 nm to 460 nm, while increased fat or lipid content present in the nerve cells may make the nerve cells susceptible to laser absorption at wavelengths between 690 nm to 710 nm, as well as those close to 980 nm in the infra-red (IR) region. The 980 nm laser wavelength is widely used for liposuction laser surgery but not for pain relief. Hence at all these wavelengths of laser, a similar destructive process affecting the C pain fibers can occur resulting in pain relief when such wavelengths are used in a laser generator as described in this invention with the resulting laser delivered at their intended anatomical targets which produce pain, as described in the cross-referenced applications.

Accordingly, in some implementations, the low level laser generator is configured to generate a laser with the following features, for application to small animals (e.g., cats and dogs) and to humans. For example, in some implementations, the low level laser generator is configured to generate a laser with wavelength between 700 nm to 705 nm laser. In other implementations, the low level laser generator is configured to generate a laser with a wavelength between 440 nm and 460 nm, and finite wavelengths above 980 nm. For example, a laser with finite wavelengths above 980 nm may be used for laser absorption by lipids, which are abundant in nerve cells. In some implementations, other wavelengths may also be used.

In some implementations, the laser has an average output power between 4 mW and 6 mW, with a range between 1 mW to 6 mW. The laser may have a pulse width on the order of nanoseconds or picoseconds that is matched with an appropriate frequency on the order of megahertz (MHz) or higher. The laser is also time controlled, for example between five seconds and ten seconds, but other time periods are also possible.

In some implementations, the laser generator is used in large animals, such as horses, cows or big cats in captivity. In such cases, the average power output of the laser may vary between 7 mW and 500 mW based on the proportionate weight of the animal, as described in greater detail in the following sections.

The low intensity laser generator described within this disclosure is configured to produce cell resonance within nerve cells to selectively cause destruction of the nerve cells without affecting the surrounding tissues. The selection of the laser wavelength depends on the absorption characteristics of the targeted nerve cells. In some cases, heat may not be generated for selective destruction of the targeted nerve cells. Instead, cell resonance may cause the selective destruction rather than heat coagulation.

FIG. 1 illustrates a schematic diagram of an example laser generator 100. As represented in FIG. 1, the laser generator 100 includes internal components for generating a low intensity laser for performing DT-LILNA. The laser generator 100 includes a power source 110, an electronic modulator 120, a micro-controller 130, an electronic timer controller 140, a laser unit 150, a watchdog circuit 160, an emergency stop button 170, and a start button 180.

The power source 110, for example, a rechargeable battery, supplies power to the laser generator 100. The electronic modulator 120, which is included in the micro-controller 130, enables generation of high-speed lasers with pulse in nanoseconds or faster. In some implementations, the electronic modulator 120 may also generate non-pulsed continuous power outputs in addition to generating pulsed power outputs. The micro-controller 130 allows a user to control the laser generated by the modulator 120 by configuring the modulator 120 to either generate a pulsed or a non-pulsed power output.

In some implementations, the modulator 120 is used to reduce the average power output of the laser unit 150 by pulsating the laser 156 and thereby decreasing the corresponding heat generated by the laser unit 150.

The electronic timer controller 140 is included within the micro-controller 130 and is activated while operating the laser generator 100 to time limit the laser delivery by the laser unit 150. The electronic timer controller 140 is activated using the start button 180.

The micro-controller 130 also includes power module 132. The micro-controller 130 uses the power module 132 to regulate the power input to the laser unit.

The laser unit 150 includes a commercial laser diode that generates a laser 156 with the wavelength between 700 and 705 nm. For example, in some implementations, the laser diode may be an Opnext HL 7001 laser diode. The laser unit 150 also includes a driver 152, which receives pulsed power outputs from the modulator 120 and enables the activation of the laser unit 150 to generate the laser 156 with a power output between 1 mW and 6 mW. In some implementations, the laser 156 may have power output between 7 mw and 42 mW, e.g., during treatment of large animals such as horses. In some other implementations, the laser 156 may have power in the range of 500 mW, e.g., during treatment of large wild animals such as elephants. The laser 156 can also be simultaneously pulsed with pulse widths shorter than nanosecond pulse durations.

The watchdog circuit 160 monitors the health of the various electronic apparatuses of the laser generator 100 and interrupts generation of the laser 156 when the operating parameters of the laser generator 100 exceed configured threshold values, and thereby ensures safe operation of the laser generator 100. For example, the watchdog circuit is activated when the timer controller 140 fails and the laser delivery time exceeds the set limit. In such an example, when the watchdog circuit 160 is activated, the power source 110 is disabled, and output of the laser 156 is terminated with immediate effect. The emergency stop button 170 is included in the laser generator 100 as an added precaution. This allows an operator of the laser generator 100 (e.g., a physician, a healthcare provider or equivalent user) to manually disable the power source 110 by pressing the button 170 to immediately shut off the laser generator 100.

The fiber optic attachment port 154 is attached to the laser unit 150 and is the starting point of the fiber optic transmission of the laser 156. The fiber optic attachment port 154 is attached to the proximal end of a fiber optic delivery system using the fiber optic transmission connection 158. The fiber optic attachment port 154 may connect to standard fiber attachments such as, for example, the SMA 905 type. In some implementations, the fiber optic attachment port 154 may connect to a custom non-standard size fiber attachment, e.g., to prevent cross connection of fibers of other medical or non-medical devices. The attachment of the fiber optic delivery system to the fiber optic attachment port 154 allows the distal delivery of the laser 156 in target tissue.

Figure 2A:
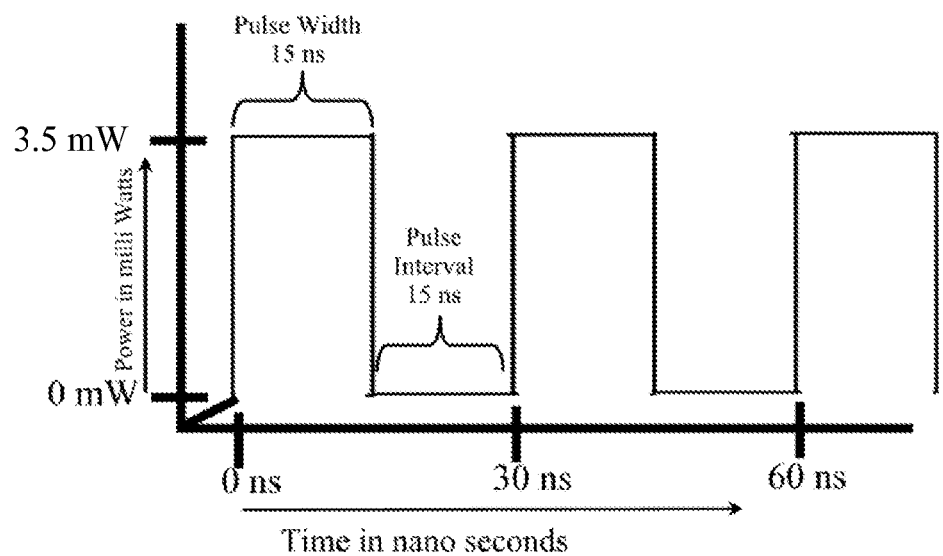
FIGS. 2A-2B are graphical representations of pulse waves generated by a laser generator for use on humans and small animals.
Figure 2B:
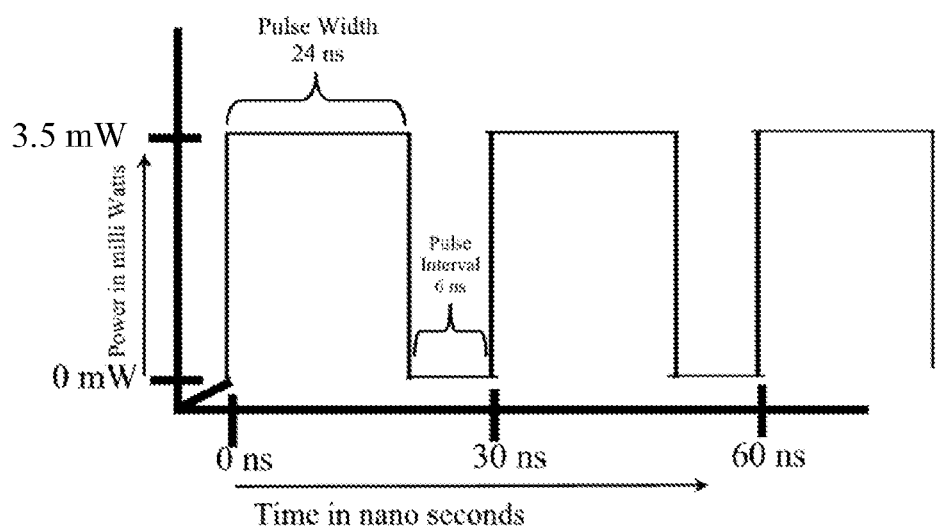

In some implementations, the laser generator 100 is adapted for use with small animals such as cats and dogs with smaller weights than humans. For example, the average weight of dogs, depending on breed and age, ranges from around 7 pounds (lbs) (approximately 3 kilograms) to over 220 lbs (approximately 100 kilograms) compared to the average weight of a human, which is in the range of 154 lbs (around 70 kilograms), with some humans weighing as much as 400 lbs (around 182 kilograms). When applied to small animals, the laser generator 100 is used to generate a laser 156 with an average laser power output range between 1 mW to 6 mW, with an optimal power output at 4.5 mW, to provide both instantaneous and long-term pain relief in small animals. Corresponding pulse waves generated by the laser generator 100 for use on humans and small animals is represented in FIGS. 2A-2B. In this context, a small animal is an animal that has an average weight within 500 lbs (around 227 kilograms).

Figure 3A:
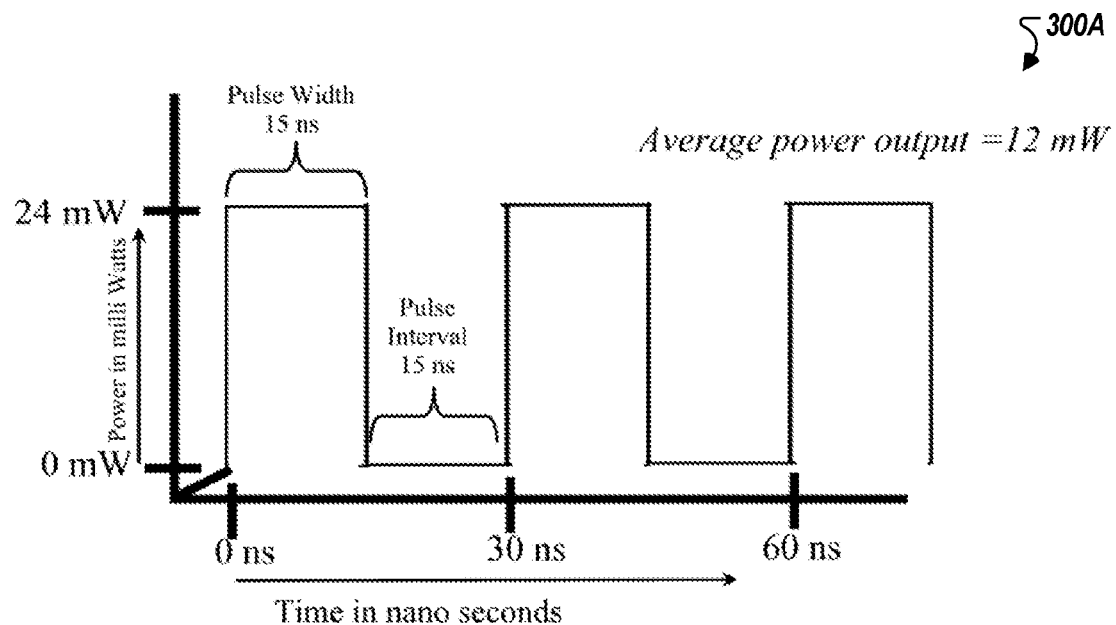
FIGS. 3A-3B are graphical representations of pulse waves generated by a laser generator for use on large animals.
Figure 3B:
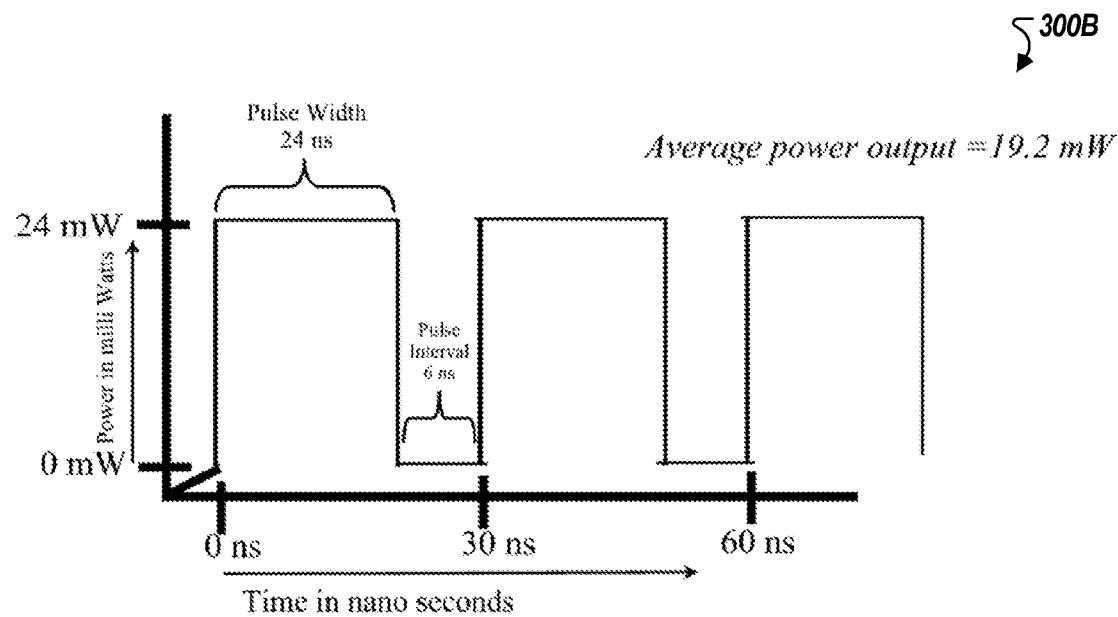

In some implementations, the laser generator 100 is adapted for use with larger animals, such as horses, cows or big cats as noted previously. In this context, a large animal is an animal that has an average weight in above 500 lbs (around 227 kilograms). In such implementations, the laser power output of the laser generator 100 is based on the proportionate weight of the animal compared to the average weight of an adult human. For example, the average weight of an adult horse is around 992 lbs (450 kilograms), which is at least six times greater than the average weight of a human. In such cases, e.g., when used in horses, the laser generator 150 may generate a laser 156 with an average laser power output range between 7 mW and 42 mW, with an optimal power output between 24 mW and 36 mW. Corresponding pulse waves generated by the laser generator 100 for use on horses is represented in FIGS. 3A-3B. In such cases, the laser generator is configured to generate a laser with wavelength characteristics similar to that of humans or small animals, e.g., between 700 nm to 705 nm, or between 440 nm and 460 nm, or finite wavelengths above 900 nm, e.g., at 980 nm. The laser may have a pulse width on the order of nanoseconds or picoseconds that is matched with an appropriate frequency on the order of megahertz (MHz) or higher. The laser is also time controlled, for example between five seconds and ten seconds, but other time periods are also possible.

In some implementations, proportional weight of other large animals, such as elephants, giraffes, or other animals kept in captivity within a zoo or a similar environment, compared to the average weight of horses is used to calculate average power laser power output ranges for treatment of these animals. For example, an elephant may weigh ten times the weight of a horse and may require an average laser power output as high as 500 mW, which approaches the upper power limit of DT-LILs for use in DT-LILT. In implementations, where the laser generator 100 is used in large animals, the laser generator 100 generates a laser 156 with an average laser output range between 7 mW to 500 mW based on the weight of the large animal.

In the implementations where the laser generator 100 is adapted for use on either small animals or large animals, the waveforms generated by the laser generator 100 for the treatment of pain have several characteristics that are similar to implementations used for humans as described previously.

In some implementations, large animals such as horses or cattle may be distinguished from very large animals such as elephants or giraffes. In such cases, a large animal is considered to be an animal that has an average weight in a range between 500 lbs and 1500 lbs (around 227 kilograms to 680 kilograms), while a very large animal is an animal that has an average weight above 1500 lbs (around 680 kilograms). In such cases, the power output for the very large animals may be much higher than for the large animals, as noted above and also described in the following sections.

FIGS. 2A-2B are graphical representations of pulse waves 200A and 200B respectively generated by the laser generator 100 for use on humans and small animals. Referring to FIG. 2A, in some implementations, the laser generator 150 generates a laser 156 with a 705 nm wavelength and power output range between 3 mW and 4.5 mW to the tip of a needle. In such implementations, the laser 156 has a 15 nanosecond pulse width, a 33 MHz high frequency pulsation, with an average power delivery of 1.75 mW at the needle tip with a peak power of 3.5 mW.

Referring now to FIG. 2B, in some implementations, the laser generator 150 generates a laser 156 that has a 24 nanosecond pulse width and a 33 MHz high frequency pulsation with an average power delivery of 2.8 mW at the needle tip with a peak power of 3.5 mW. Comparing the pulse waves represented in FIG. 2A to that in FIG. 2B, although the peak power remains the same at 3.5 mW, the average power may be reduced based on the configurations of the pulse width and the pulse interval of the pulse waves. For example, average power output in FIG. 2A is decreased compared to the average power output in FIG. 2B by increasing the pulse interval in the former case (15 nanoseconds in FIG. 2A but 6 nanoseconds in FIG. 2B) when no energy is delivered to the target tissue.

FIGS. 3A-3B are graphical representations of pulse waves 300A and 300B respectively generated by the laser generator 100 for use on large animals. Referring to FIG. 3A, in some implementations, the laser generator 100 generates a laser 156 with a 705 nm wavelength and power output range between 1 mw and 6 mW, or between 7 mW and 24 mW, depending on the proportionate weight of the animal, to the tip of a needle. In such implementations, the laser 156 has a 15-nanosecond pulse width, a 33 MHz high frequency pulsation, with an average power delivery of 12 mW at the needle tip with a peak power being constant at 24 mW.

Referring now to FIG. 3B, in some implementations, the laser generator 150 generates a laser 156 that has a 24 nanosecond pulse width and a 33 MHz high frequency pulsation with an average power delivery of 19.2 mW at the needle tip with a peak power of 24 mW. Comparing the pulse waves represented in FIGS. 3A and 3B, although the power output range remains the same (i.e., between 1 mw and 6 mW, or between 7 mW and 24 mW) and the peak power remains at 24 mW, the average power may be reduced based on the configurations of the pulse width and the pulse interval of the pulse waves. For example, average power output in FIG. 3A is decreased compared to the average power output in FIG. 3B by increasing the pulse interval in the former case (15 nanoseconds in FIG. 3A but 6 nanoseconds in FIG. 3B) when no energy is delivered to the target tissue.

In some implementations, e.g., for treatment of very large animals such as elephants or giraffes, the peak power output for the laser in FIG. 3A or FIG. 3B is greater than the 24 mW shown, e.g., in the range of 500 mW as noted previously. In such cases, the average power delivery at the needle tip is in the range of 250 mW in FIG. 3A, and in the range of 400 mW in FIG. 3B.

The laser generator of this disclosure also has several non-specific enhancements created that are common to the use of electronic or medical devices. These includes use of an interactive touch screen by an operator, for example, a physician or other equivalent healthcare professional, to control the apparatus through software and hardware operations, and use of a foot pedal for timer-controller laser activation for convenient use.

The invention claimed is:

1. A laser generator, comprising:
    an electronic modulator that is configured to generate one of a continuous non-pulsed signal or a pulsed signal including a wavelength in a specified range;
    a laser unit that is configured to generate a laser, wherein the laser unit is coupled to the electronic modulator such that the laser generator outputs a laser that is one of a continuous non-pulsed laser power output or a pulsed laser power output, wherein the laser power output includes a wavelength in the specified range;
    an electronic timer controller that is configured to be activated during operation of the laser unit and operable to limit delivery time of the laser; and a watchdog circuit that is configured to terminate the laser power output that is output by the laser generator by interrupting power source to the laser unit in response to a determination that the electronic timer controller has failed.

2. The laser generator of claim 1, wherein the wavelength of the laser power output is between 700 nanometers (nm) and 705 nm.

3. The laser generator of claim 1, wherein the wavelength of the laser power output is between 440 to 460 nm.

4. The laser generator of claim 1, wherein the electronic modulator is configured to generate the pulsed power output including a pulse width in a range of nanoseconds, and wherein the laser generator is operable to output the pulsed laser power output including a 33 megahertz (MHz) high frequency pulsation and a pulse width that is one of 15 nanoseconds or 24 nanoseconds.

5. The laser generator of claim 4, wherein the laser generator includes a power source that is configured to output power within a range between one of 1-6 milli-watts (mW), 7-24 mW, or up to 500 mW, and wherein the range is selected based on a size of a body to be treated.

6. The laser generator of claim 5, wherein the laser generator is operable to output an average power in a range of 12 mW with a peak power in a range of 24 mW associated with the pulsed laser power output that includes the 33 MHz high frequency pulsation and the pulse width of 15 nanoseconds.

7. The laser generator of claim 5, wherein the laser generator is operable to output an average power in a range of 19.2 mW with a peak power in a range of 24 mW associated with the pulsed laser power output that includes the 33 MHz high frequency pulsation and the pulse width of 24 nanoseconds.

8. The laser generator of claim 5, wherein the power source includes a rechargeable battery.

9. The laser generator of claim 1, comprising a user interface, wherein operation of the laser generator is controllable via user inputs provided through the user interface.

10. The laser generator of claim 9, wherein the user interface includes a touchscreen user interface.

11. The laser generator of claim 1, further comprising a user-operated shutoff button for emergency shutdown.

12. The laser generator of claim 1, further comprising a microcontroller, wherein the electronic modulator and the electronic timer are included in the microcontroller.

13. The laser generator of claim 12, wherein the microcontroller includes a power unit that is configured to control an amount of power that is provided to the laser unit.

14. The laser generator of claim 13, wherein the laser unit includes a first input that is configured to receive power from the power unit, and a second input that is configured to receive one of the continuous non-pulsed signal or the pulsed signal from the electronic modulator, and wherein the laser unit is operable to output the laser power output with power in a range between one of 1-6 mW, 7-24 mW, or in a range up to 500 mW.

15. The laser generator of claim 1, wherein the electronic timer controller is operable to limit the delivery time of the laser to one of 5 seconds or 10 seconds.

16. The laser generator of claim 1, comprising a fiber port that is configured to:
    couple a fiber optic delivery system to the laser generator; and
    transmit the laser power output that is output by the laser generator to the fiber optic delivery system for delivery to a treatment area.

17. The laser generator of claim 1, wherein the specified range of the wavelength is between 690 nm and 980 nm.

18. The laser generator of claim 1, wherein the watchdog circuit is configured to perform operations comprising:
    monitoring the delivery time of the laser;
    comparing the delivery time of the laser to a predetermined threshold;
    in response to the comparing, determining whether the delivery time of the laser exceeds the predetermined threshold;
    based on determining that the delivery time of the laser exceeds the predetermined threshold, determining that the electronic timer controller has failed; and
    in response to determining that the electronic timer controller has failed, terminating the laser power output that is output by the laser generator.

19. The laser generator of claim 1, wherein the laser power output is configured for application to large animals.

20. The laser generator of claim 19, including a power source that is configured to output power proportional to the weight of the large animal.

* * * * *